United States Patent [19]

Alston

[11] 4,452,899
[45] Jun. 5, 1984

[54] METHOD FOR METERING BIOLOGICAL FLUIDS

[75] Inventor: Wilton D. Alston, Webster, N.Y.

[73] Assignee: Eastman Kodak Company, Rochester, N.Y.

[21] Appl. No.: 387,125

[22] Filed: Jun. 10, 1982

[51] Int. Cl.³ .................. G01N 1/14; G01N 35/06
[52] U.S. Cl. .................. 436/46; 73/864.11; 141/119; 422/63; 422/66; 422/100; 436/54; 436/180
[58] Field of Search .............. 436/49, 46, 43, 54, 436/179, 180, 162; 422/63, 66, 100, 70; 73/864.11–864.18, 61.1 C; 222/571; 141/117, 119

[56] References Cited

U.S. PATENT DOCUMENTS

| | | | |
|---|---|---|---|
| 3,484,024 | 12/1969 | Jones et al. | 222/571 |
| 4,000,974 | 1/1977 | Acord | 436/49 |
| 4,340,390 | 7/1982 | Collins et al. | 422/64 |
| 4,347,875 | 9/1982 | Columbus | 73/864.11 |

Primary Examiner—Michael S. Marcus
Attorney, Agent, or Firm—Dana M. Schmidt

[57] ABSTRACT

A method is disclosed for repeatedly and accurately depositing predetermined amounts of fluid, especially biological fluids, onto generally planar analysis slides. Fluid is aspirated into a disposable metering tip which is rapidly moved into a metering position where the fluid is expelled onto a slide. During movement of the tip into the metering position, a partial vacuum is created on the fluid in the tip, causing the fluid to be drawn up into the tip and thereby preventing fluid from being prematurely expelled onto the slide.

10 Claims, 9 Drawing Figures

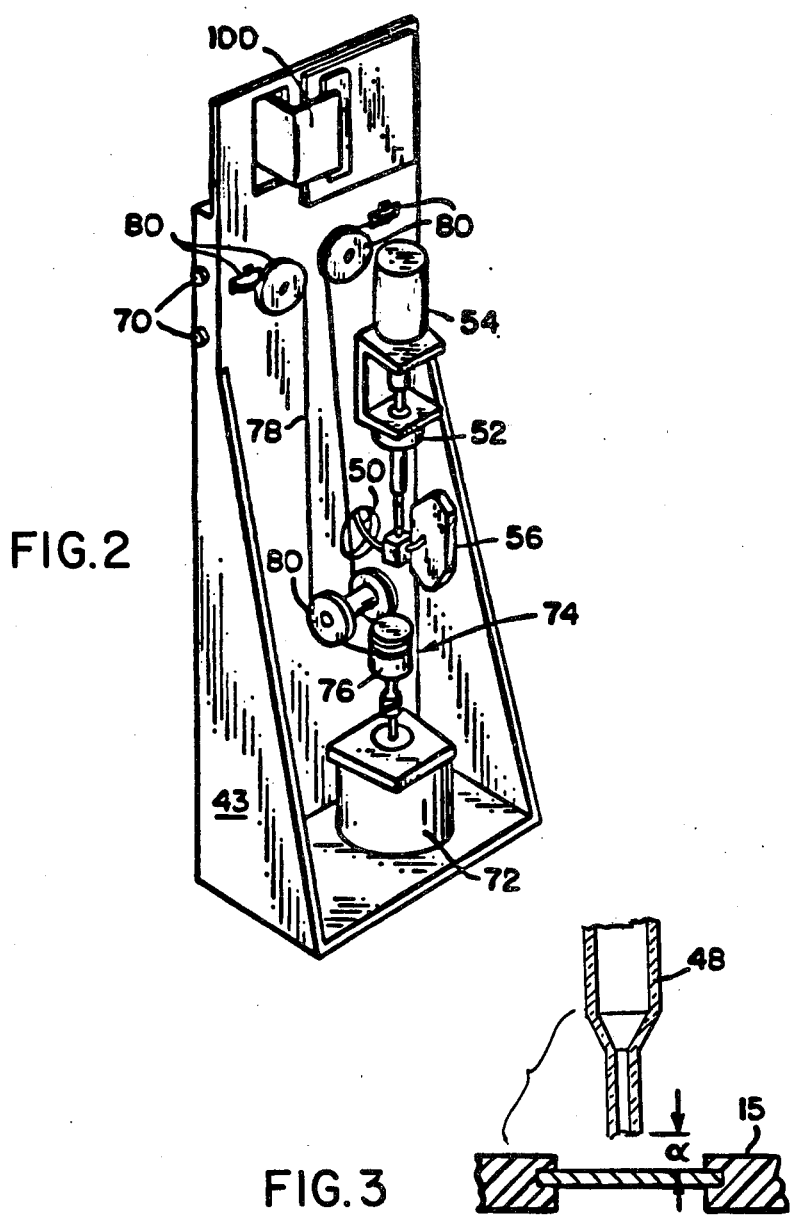

METHOD FOR METERING BIOLOGICAL FLUIDS

CROSS-REFERENCES TO RELATED APPLICATIONS

Reference is made to commonly-assigned U.S. patent application Ser. No. 260,855, entitled Method and Apparatus for Metering Biological Fluids, filed in the name of Collins et al., on May 1, 1981, now U.S. Pat. No. 4,340,390.

BACKGROUND OF THE INVENTION

1. Field of the Invention

This invention relates to the chemical analysis of substances, and more particularly, to a method for the precise metering of biological fluids onto test elements.

2. State of the Prior Art

A number of automated systems have been developed for performing quantitative chemical analyses of fluid samples. Most of the commercially-available systems utilize liquid reagents and require analyzer equipment having intricate solution handling and transport capabilities. Recent developments, however, have provided test elements in essentially planar, dry form which can be loaded into a cartridge for use in an analyzer. In the use of such an analyzer, a test element from a cartridge is fed into a metering station where a predetermined amount of sample fluid is deposited on the test element. After an incubation period, the element is moved to a read station where a change in the test element is measured, the amount of change being proportional to a particular analyte in the fluid. The test element is used only once and is discarded after the reading has been taken. An analyzer for use with such test elements is disclosed in commonly-assigned U.S. Pat. No. 4,152,390.

Test elements of the type described above are adapted to function with very small quantities of sample fluid. For example, test elements for performing colorimetric analyses can produce a measurable response with only 10 microliters of sample fluid, and elements for performing potentiometric analyses are operable with 10 microliters of sample fluid and 10 microliters of reference fluid. The volume of fluid supplied to the elements should preferably not vary more than 5% from a selected value to achieve desirable test results. Thus, there is a problem in providing a metering device which can deliver precise micro quantities of fluid, in spite of variations in the physical properties of the fluid and the test elements. Moreover, in high-throughput analyzers, the metering device must be capable of repeatedly and accurately dispensing such quantities of fluid onto the test elements as they are sequentially moved into a metering station.

In European Patent Application No. 400940.3, Pub. No. 0042337, published Dec. 23, 1981, there is disclosed a method and apparatus for the precise metering of biological fluids onto generally planar test elements, or analysis slides. The apparatus comprises a dispenser which is adapted to pick up a disposable metering tip, aspirate fluid into the tip, meter a predetermined amount of fluid from the tip onto an analysis slide, and eject the tip after the metering operation. In the use of such metering apparatus in a high-throughput analyzer, the metering device must be rapidly moved from the aspiration station to the metering position where the fluid is deposited on an analysis slide; best results are obtained if the metering tip is moved closely adjacent the slide, preferably within a space between about 0.030 cm and about 0.15 cm from the slide. However, a problem occurs if a tip containing fluid is rapidly moved toward a slide and then stopped suddenly in a position closely adjacent the slide. When the metering tip is stopped suddenly, fluid within the metering tip tends to momentarily protrude from the tip due to the effect of inertia on the fluid; if the tip is close enough to the slide when it is stopped, the protruding fluid will contact the slide and a condition known as "pre-spot" occurs in which a certain amount of fluid is deposited on the slide. Such a condition is undesirable, since it tends to produce uneven distribution of fluid on the slide which causes inaccurate test results.

SUMMARY OF THE INVENTION

It is an object of the present invention to overcome the above-described problem in prior-art devices, and to provide a novel method for the repeated, precise dispensing of micro quantities of fluid onto test elements for the analysis of biological fluids. The invention is particularly applicable to the metering of biological fluids onto generally planar test elements, or analysis slides, in high-throughput apparatus in which the metering tip is rapidly moved into the metering position.

In accordance with one aspect of the invention there is provided a process for the precise dispensing of a biological fluid from a metering tip onto a generally planar analysis slide, the process comprising the steps of: introducing a quantity of fluid into the tip, said tip having an air space above the fluid; moving the tip toward a metering position; creating a partial vacuum on the fluid in the tip when the tip is at a point spaced from the metering position; moving the tip into the metering position; pressurizing the air and fluid in the tip for a preselected period to force a selected volume of fluid onto the slide at a predetermined dispense rate; and maintaining the tip briefly in the metering position after the period and then withdrawing the tip from the metering position.

The process of the subject invention can be performed using apparatus which comprises a dispenser supported on a carriage mounted for lateral movement. The dispenser is movable vertically relative to the carriage by means of a rack-and-pinion drive. The dispenser is connected to a positive displacement pump which is adapted to effect the aspiration of fluid into the dispenser and the expelling of fluid therefrom. At the start of a metering cycle, the carriage is moved to locate the dispenser over a waste receptacle where the metering tip from the preceding metering cycle is ejected. The dispenser then picks up a new metering tip, and a supply of sample fluid is aspirated into the tip. The dispenser is then moved to position the tip in a metering position where a predetermined amount of sample fluid is deposited onto an analysis slide; the dispenser is then elevated to a "home" position to complete the metering cycle.

BRIEF DESCRIPTION OF THE DRAWINGS

FIG. 2 is a perspective view of a pump for the dispenser and a drive mechanism for the carriage;

FIG. 3 is an enlarged fragmentary elevational view, in section, showing a metering tip in the metering position over an analysis slide;

The invention is described hereinafter in connection with performing quantitative chemical analyses of biological fluids, such as blood serum. However, the invention is not so limited, and it can also be employed in other applications where precise metering is required. Although the dispensing of blood sera is described hereinafter by way of example, the invention may be used in dispensing other fluids.

One form of test element, or analysis slide, for use with the subject invention is disclosed in the commonly-owned U.S. Patent to Pryzbylowicz et al., U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid. Another form of test element for use with the disclosed invention is shown in the patent to Hamblen et al., U.S. Pat. No. 4,053,381, granted Oct. 11, 1977. This patent describes a test element, or analysis slide, of the type which is used to potentiometrically designate the activity of ions in a liquid test solution by the use of electrodes.

Terms such as "up," "down," "lower," "vertical," "horizontal," and "bottom," as used herein, refer to the orientation of parts when the disclosed apparatus is positioned in its customary position of use.

"Pre-spot" as used herein refers to a condition in which a quantity of sample fluid from a metering tip is deposited on an analysis slide, prior to a normal metering cycle, as a result of fluid protruding from the tip during positioning of the tip in the metering position.

The sera to be dispensed are to be tested by devices requiring very accurate, small volumes of sera. The volumes to be dispensed are substantially fixed for a particular application and range from 1 to about 30 microliters, and preferably between about 8 and about 13 microliters. Such small volumes permit the performance of multiple tests on a relatively small volume of serum from a patient; in the case of elderly or infant patients, only small volume of blood are available for testing, and the smaller the volume needed for each test, the greater the number of tests which can be run on a given sample of serum.

Figure 1:
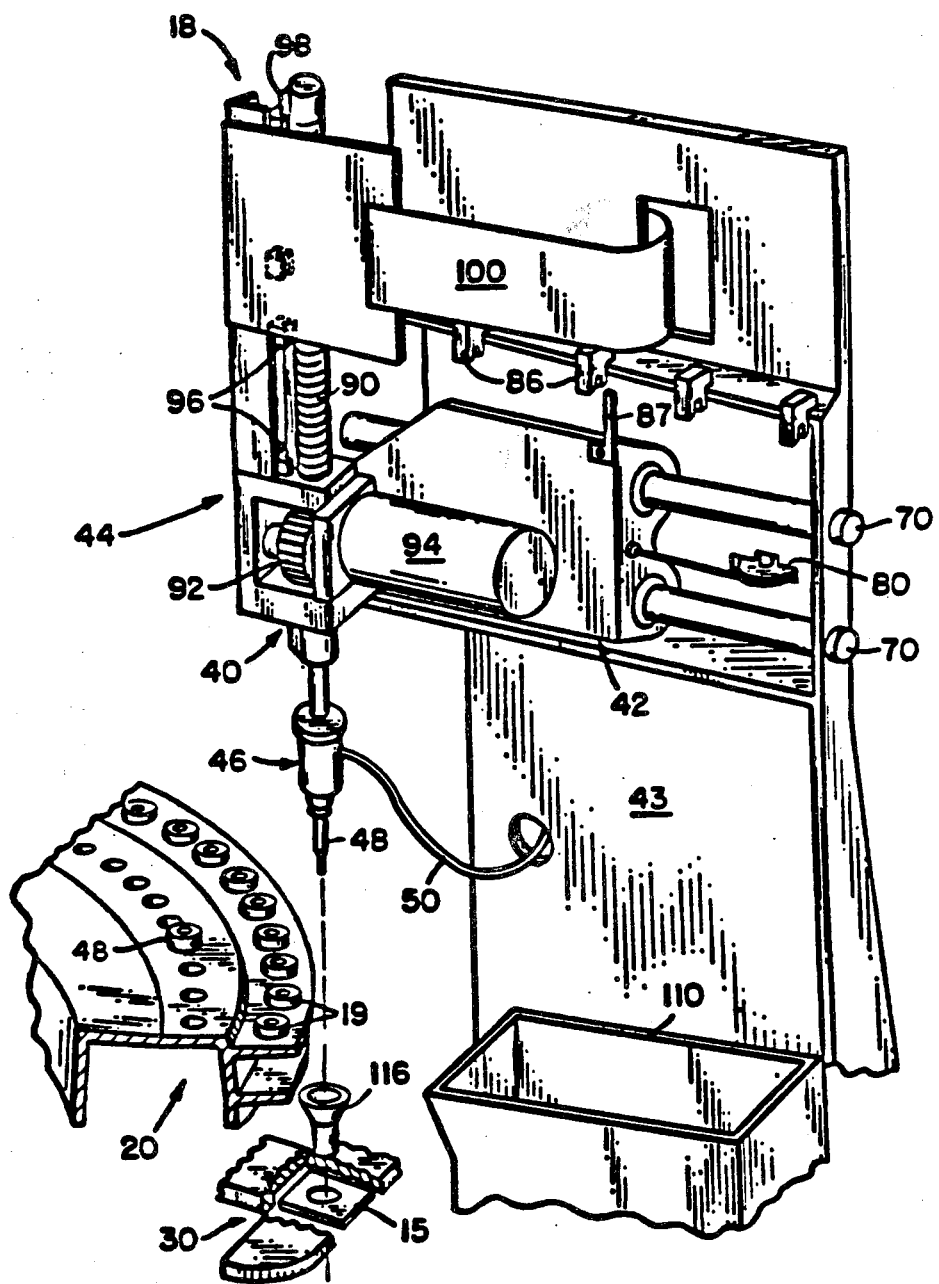
FIG. 1 is a perspective view of metering apparatus used in performing the method described herein, showing the dispenser and the carriage for the dispenser.

With reference to FIG. 1, there is shown metering apparatus 18 which is adapted to aspirate sample fluid from a cup 19 supported in a sample tray 20 and to deposit a predetermined amount of the fluid onto an analysis slide 15 supported in a slide distributor 30. Metering apparatus 18 is adapted to be used in an analyzer, as disclosed, for example, in the aforesaid European Patent Application No. 81400940.3. After the metering operation, the analysis slide 15 is deposited in an incubator (not shown); after an appropriate period of incubation, the slide 15 is read by an analysis means (not shown) adapted to measure a change in the slide as a result of the fluid deposited thereon. Metering apparatus 18 comprises a dispenser 40, and a means for positioning dispenser 40 which includes a carriage 42 for moving dispenser 40 laterally through a plurality of stations and a vertical drive 44 for raising and lowering dispenser 40 at each of the stations. Dispenser 40 comprises a dispenser head 46 which is adapted to receive a disposable metering tip 48, and is connected by means of a line 50 to a pump 52 (FIG. 2) of the positive displacement type. Pump 52 comprises a piston, not shown, which is driven by a bidirectional stepper motor 54.

When motor 54 is actuated in one direction, a partial vacuum is created in line 50 by pump 52, and fluid is drawn into tip 48 until the tip is partially filled. Motor 54 is actuated in an opposite direction to meter fluid from tip 48. In the metering operation, motor 54 drives pump 52 for a preselected period during which the pressure in line 50 and tip 48 is raised sufficiently to force about 10 µl of fluid onto an analysis slide. Under certain operating conditions, depending on the amount of fluid aspirated into tip 48, it may be desirable to vent line 50 before dispensing fluid onto an analysis slide. A pressure transducer 56 closely monitors pressure in line 50 for purposes which will be explained in more detail hereinafter.

Sample tray 20 is adapted to carry a disposable tip 48 for each of the sample fluids to be analyzed. A new tip 48 is used with each sample fluid to avoid any cross-contamination problems. The cups 19 containing sample fluid are arranged around the outer periphery of tray 20, as shown in FIG. 1. An indexing mechanism, not shown, advances tray 20 at the start of each metering cycle to bring a cup 19 and new tip 48 respectively into the aspiration station and the-tip supply station for cooperation with metering apparatus 18. Tips 48 can be formed by known molding techniques from polymers, such as acetal and polypropylene. One tip which is particularly suitable for use in apparatus 18 is the tip described and claimed in commonly-owned U.S. Application Ser. No. 168,789, filed on July 14, 1980, by R. L. Columbus, entitled "Self Cleaning Nozzle Construction for Aspirators." Also, certain commercially-available pipette tips have metering characteristics which are acceptable for use in apparatus 18. One example of such a tip is the Elkay #000-000-01C tip, manufactured by Elkay Products, Inc., Worcester, Mass.

Carriage 42 is mounted for horizontal movement on two parallel support rods 70. Rods 70 are carried on a pylon 43 attached to the analyzer frame, not shown. A drive means for carriage 42 includes a bidirectional stepper motor 72 (FIG. 2) which is connected to a capstan drive 74. Drive 74 comprises a drum 76; a cable 78 carried on drum 76 is supported on guide pulleys 80 and connected to carriage 42. It will be seen from FIGS. 1 and 2, that when motor 72 is driven, for example, in a counterclockwise direction, as viewed in FIG. 2, carriage 42 will move to the right (FIG. 1). Carriage 42 must be located along a line at four points which include the tip supply station, the aspiration station, the metering station and the tip-eject station. Four horizontal-position sensors 86 of a photoelectric type cooperate with a flag 87 on carriage 42 to precisely position the carriage 42 at each of these stations.

Vertical drive 44 comprises a rack 90 which is attached to dispenser head 46. Rack 90 is raised and lowered by means of a pinion 92 driven by a stepper motor 94 mounted on carriage 42. Four vertical-position sensors 96 cooperate with a flag 98 on rack 90 to precisely determine the vertical position of dispenser head 46. Power from a power supply, not shown, is supplied to the sensors 96 and motor 94 through a ribbon cable 100.

In the operation of metering apparatus 18, dispenser 40 is moved through at least one complete metering cycle for each sample fluid processed. At the start of the metering cycle, carriage 42 is moved to the tip-eject station to position dispenser 40 over a waste receptacle 110 where a metering tip 48 from a previous metering cycle is ejected into the receptacle 110 by an ejector, not shown, on head 46. Carriage 42 is then moved by motor 72 to the tip-supply station where dispenser 40 is located directly over a disposable tip 48 in sample tray 20. Dispenser 40 is then lowered to pick up a tip 48, raised, and moved laterally to the aspiration station.

At the aspiration station, dispenser 40 is lowered to locate a tip 48 in a sample cup 19 where it aspirates sufficient sample fluid to perform the number of tests desired. After aspiration and before withdrawal of the tip 48, approximately 10 μl of fluid are dispensed back into cup 19; this primes the dispenser and insures that the first analysis slide 15 will receive a precise amount of fluid. The dispenser 40 is then raised, moved laterally to the metering station where tip 48 is positioned directly over an analysis slide 15; tip 48 is then lowered into a guide 116 (FIG. 1) on distributor 30 which locates the tip 48 in the metering position. When the tip 48 is in the metering position, pump 52 is actuated to increase the pressure in the tip sufficiently above ambient to force about 10 μl of fluid from the tip.

Figure 5A:
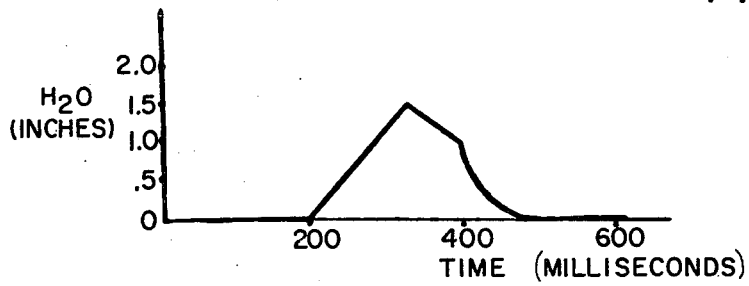
FIG. 5a is a graph illustrating the pressure profile of the fluid within the metering tip during one mode of operation.
Figure 5B:
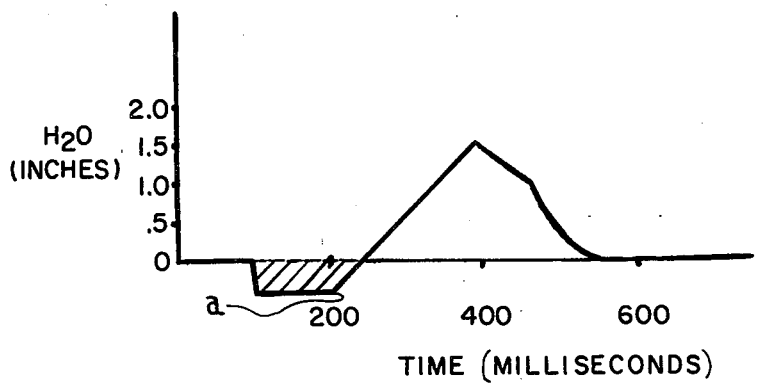
FIG. 5b is a graph similar to FIG. 5a, but showing the pressure profile of the fluid within a metering tip during performance of the method of metering disclosed herein.

Apparatus 18 is operable in one mode in which pump 52 is driven in a first direction to aspirate fluid into tip 48, stopped while tip 48 is moved into the metering position, and driven in an opposite direction to meter fluid from tip 48; the pressure profile of fluid in tip 48 during such a mode of operation is as shown in FIG. 5a. For reasons which will be apparent hereinafter, apparatus 18 is operated in a different mode in performing the steps of the invention described herein; operation in this different mode results in a pressure profile as shown in FIG. 5b.

Figure 4A:
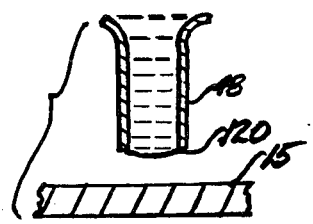
FIG. 4a is an enlarged fragmentary elevational view, in section, showing the metering tip and fluid contained therein as it approaches an analysis slide.
Figure 4B:
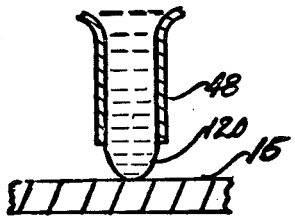
FIG. 4b is a view similar to FIG. 4a, but with the metering tip in the metering position and showing the fluid protruding from the tip.
Figure 4C:
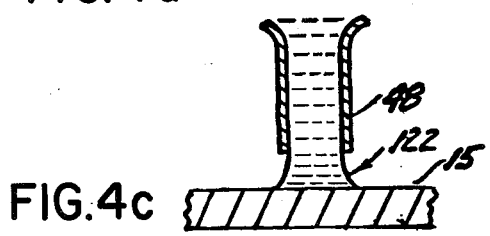
FIG. 4c is a view similar to FIG. 4a and FIG. 4b, but showing the flow of the fluid after it contacts the analysis slide.

Dispenser 40 must be rapidly moved through the metering cycle when apparatus 18 is used in a high-throughput analyzer (not shown). For example, when tip 48 is being lowered into the metering position, the tip 48 is moving at a rate between about 1.5 inches per second and about 6 inches per second. When a tip 48 containing fluid is rapidly moved toward an analysis slide and then stopped abruptly in guide 116, fluid in tip 48 tends to protrude from tip 48 for a brief period of time before being drawn back into the tube by the surface tension and capillary attraction on the fluid. The action of the fluid in tip 48 during positioning of tip 48, in the absence of any means to control the fluid, is shown in FIGS. 4a–4c. In FIG. 4a, tip 48 is shown as it approaches a slide 15; the fluid has a meniscus 120. Just after tip 48 is seated in guide 116 on distributor 30, the meniscus 120 assumes the shape shown in FIG. 4b due to the inertial effect on the fluid. If the fluid contacts slide 15, it tends to spread out, as shown at 122 in FIG. 4c, prior to being severed from the main body of fluid in tip 48. When the fluid contacts slide 15, a certain quantity of fluid remains on the slide which results in a pre-spot.

Figure 4D:
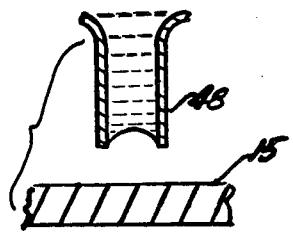
FIG. 4d is a view similar to FIG. 4a, but showing the position of the fluid within the metering tip after the reversal of the metering pump.

To avoid the pre-spot described above, motor 54 is actuated to drive pump 42 in a reverse direction as tip 48 approaches the metering position; this creates a partial vacuum in line 50 and causes the fluid to be drawn up into tip 48, as shown in FIG. 4d. The pressure profile of the fluid in the metering tip when a partial vacuum is drawn during positioning of the tip is as shown in FIG. 5b. A partial vacuum of approximately 0.4 inches of water (cross-hatched portion of FIG. 5b) is created in the fluid in tip 48 by driving motor 54 for about 8 steps in the direction to reverse pump 52. The partial vacuum is created on the fluid in tip 48 just prior to the point at which tip 48 seats in guide 116 in the metering position, for example ¼ to ½ inch above the metering position. When tip 48 reaches the metering position, the motor 54 is actuated to start the metering operation.

It has been found that in cases where the pre-spot condition exists, precision is affected, even if the desired volume of fluid is metered on the slide. That is, precision is affected, even if the volume of the pre-spot plus the volume subsequently metered on the slide during the normal metering cycle is equal to the desired volume of fluid. This is particularly true for analysis slides having a dye incorporated in the spreading layer, for example a slide for the analysis of amylase as disclosed in U.S. Pat. No. 4,144,306, issued on Mar. 13, 1979. In such a slide, a pre spot will cause a certain amount of dye from the spreading layer to start to penetrate into the other layers. When additional fluid is deposited on the slide, more dye is released from the spreading layer; however, the dye distribution is likely to be uneven. The uneven dye distribution is known as "targeting" and adversely affects the test results.

When tip 48 is in the metering position, pump 52 is actuated for a preselected period to meter the desired amount of sample fluid onto the analysis slide 15. With reference to the pressure profile shown in FIG. 5b, the metering of fluid starts from a point designated "a" and continues for about 400 milliseconds. Tip 48 remains in the metering position for a predetermined time after pump 52 stops to complete the metering operation; then dispenser 40 is raised to a "home" position, shown in FIG. 1. In most cases, more than one analysis will be performed per sample fluid. If additional analyses are being performed, the dispenser 40 will be raised and lowered for each new slide 15. Each time the tip is lowered into the metering position a partial vacuum is drawn to avoid the pre-spot condition.

Metering apparatus 18 is particularly suitable for use with biological fluids, e.g. blood serum having a surface tension which varies between about 28 dynes/cm and about 75 dynes/cm and a relative viscosity between about 0.8 and about 3 (compared to distilled water). Apparatus 18 is adapted to dispense these fluids such that the mean metered volume does not vary more than 5% from a selected value, and the precision, expressed as a coefficient of variation, is less than 5%. To achieve these results, metering apparatus 18 preferably has the properties listed below.

1. There should be no separation of the fluid stream during the metering operation. To make sure that separation does not occur it, has been found that the spacing α of tip 48 from slide 15 (see FIG. 3) is preferably between about 0.012 inches (0.030 cm) and about 0.060 inches (0.15 cm).

2. It is also preferred that the dispense rate at which fluid is expelled from tip 48 is between about 10 $\mu$l/sec and about 300 $\mu$l/sec. If the dispense rate is too slow, there is danger of separation of the fluid stream, even with proper spacing of tip 48 from slide 15; if the rate is too fast, fluid tends to build up around tip 48. A representative rate within this range is 50 $\mu$l/sec, which can be used regardless of the type or chemistry of the slide onto which the fluid is being metered. That is, this fixed, predetermined rate has been used both on colorimetric type slides, e.g. glucose, BUN, or a like assay, as well as on potentiometric slides, e.g. a NA+ assay.

3. At the completion of the dispensing of fluid, i.e. after pump 52 has stopped, it is preferred that tip 48 dwell in the metering position (FIG. 3) between about 0.05 sec and about 0.5 second before being withdrawn. This insures that there will be a clean break of the stream of fluid upon withdrawal; if the tip 48 dwells for a greater period of time, fluid may be pulled out of tip 48 by the slide.

4. After the dwell time as noted above, it is preferred that tip 48 be withdrawn from the metering position at a rate of between about 0.2 inches/sec (0.5 cm/sec) and about 2 inches/sec (5.08 cm/sec). The tip 48 is withdrawn at a relatively slow rate to allow a "fluid wipe-off" effect.

In the use of the disclosed metering apparatus with a high-throughput analyzer (not shown) a metering operation takes place approximately every 12 seconds. Thus, it will be seen that each of the steps in the metering cycle must be carefully controlled and monitored, and metering apparatus 18 must function in timed relation to the other elements of the analyzer. Pressure transducer 56 is used to monitor the performance of apparatus 18. Pressure is sensed in line 50, and if conditions are present such as a plugged tip 48, no fluid in cup 19, or a separation of the fluid stream between the tip 48 and the slide 15, they will be detected by the transducer. A control system (not shown) for metering apparatus 18 could include one or more computers which may take any of the various forms known in the art that include programmable microcomputers. The instructions and method of programming such computers is well known in the art, and thus, no further explanation is considered necessary.

The invention has been described in detail with reference to certain preferred embodiments thereof, but it will be understood that variations and modifications can be effected within the spirit and scope of the invention.

What is claimed is:

1. A process for the precise dispensing of a biological fluid from a metering tip onto a generally planar analysis slide, said process comprising the steps of:
 introducing a quantity of fluid into said tip, said tip having an air space above the fluid;
 moving the tip toward a metering position in which the tip is spaced between about 0.030 cm and about 0.15 cm from an analysis slide;
 creating a partial vacuum on the fluid in the tip when the tip is at a point spaced from the metering position in an amount effective to prevent pre-spotting when the tip is moved into the metering position;
 moving the tip into the metering position at a velocity that would cause pre-spotting in the absence of the partial vacuum;
 pressurizing the air and fluid in the tip for a preselected period to force a selected volume of fluid onto the slide at a predetermined dispense rate; and
 maintaining said tip briefly in the metering position after said period and then withdrawing the tip from said metering position.

2. A process, as defined in claim 1, wherein the air space above said fluid is vented to the atmosphere, before creating a partial vacuum on the fluid.

3. A process, as defined in claim 1, wherein said partial vacuum is equal to about 0.4 inches of water.

4. A process, as defined in claim 1, wherein said air and fluid are pressurized to about 1.5 inches of water in forcing the 10 $\mu$l of fluid onto the slide.

5. A process, as defined in claim 1, wherein said selected volume is about 10 $\mu$l.

6. A process, as defined in claim 1, wherein said dispense rate is between about 10 $\mu$l/sec and 300 $\mu$l/sec.

7. A process, as defined in claim 1, wherein said tip is maintained in said metering position between about 0.05 sec and about 0.5 sec.

8. A process, as defined in claim 1, wherein said tip is withdrawn from the metering position at the rate of between about 0.5 cm/sec and about 5.08 cm/sec.

9. A process, as defined in claim 1, wherein a positive displacement pump is used to introduce fluid into the tip and create said vacuum, said pump having a piston which is movable through a first distance in one direction to aspirate said fluid and an additional distance in said direction to create said vacuum.

10. A process, as defined in claim 1, wherein said point spaced from the metering position is between about ¼" and about ½" from the metering position.

* * * * *